(12) United States Patent
Koblish et al.

(10) Patent No.: US 6,468,272 B1
(45) Date of Patent: Oct. 22, 2002

(54) SURGICAL PROBE FOR SUPPORTING DIAGNOSTIC AND THERAPEUTIC ELEMENTS IN CONTACT WITH TISSUE IN OR AROUND BODY ORIFICES

(75) Inventors: Josef V. Koblish, Palo Alto; David K. Swanson, Mountain View; Huy D. Phan; Edward J. Snyder, both of San Jose, all of CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/447,185

(22) Filed: Nov. 22, 1999

Related U.S. Application Data

(63) Continuation-in-part of application No. 09/072,872, filed on May 5, 1998, now Pat. No. 6,142,994, and a continuation-in-part of application No. 08/949,117, filed on Oct. 10, 1997, now Pat. No. 6,152,920.

(51) Int. Cl.[7] .................................................. A61B 18/14
(52) U.S. Cl. ........................ 606/41; 606/46; 606/47; 606/49; 600/374; 600/393; 607/99
(58) Field of Search ............................. 606/41, 46, 47, 606/49; 607/99; 600/374, 393; 604/105

(56) References Cited

U.S. PATENT DOCUMENTS

| 463,785 A | 11/1891 | Connable |
|---|---|---|
| 1,519,018 A | 12/1924 | Bodreau |
| 2,976,888 A | 3/1961 | Merriman |
| 3,316,913 A | 5/1967 | Swenson |
| 3,730,187 A | 5/1973 | Reynolds |
| 3,999,555 A | 12/1976 | Person |
| 4,011,872 A | 3/1977 | Komiya |
| 4,181,131 A | 1/1980 | Ogiu |
| 4,306,561 A | 12/1981 | de Medinaceli |
| 4,493,320 A | 1/1985 | Treat |
| 4,517,975 A | 5/1985 | Garito et al. |
| 4,523,679 A | 6/1985 | Paikoff et al. |
| 4,532,924 A | 8/1985 | Auth et al. |
| 4,565,200 A | 1/1986 | Cosman |
| 4,567,890 A | 2/1986 | Otha |

(List continued on next page.)

FOREIGN PATENT DOCUMENTS

| DE | 4425195 | 11/1995 |
|---|---|---|
| DE | 19503702 | 8/1996 |
| EP | 0 484 671 A2 | 5/1992 |
| EP | 0 584 787 A1 | 8/1992 |
| EP | 1042990 A1 | 10/2000 |
| WO | WO 93/08755 | 5/1993 |
| WO | WO 95/10236 | 4/1995 |
| WO | WO 96/37156 | 11/1996 |
| WO | WO 97/17027 | 5/1997 |
| WO | WO 97/30644 | 8/1997 |
| WO | WO 97/41793 | 11/1997 |
| WO | WO 98/17187 | 4/1998 |
| WO | WO 98/26724 | 6/1998 |
| WO | WO 99/04696 | 2/1999 |
| WO | WO 99/18878 | 4/1999 |
| WO | WO99/34741 | 7/1999 |
| WO | WO 01/80724 A2 | 11/2001 |

OTHER PUBLICATIONS

US 5,688,268, 11/1997, Billings (withdrawn)

*Primary Examiner*—Lee Cohen
(74) *Attorney, Agent, or Firm*—Henricks, Slavin & Holmes LLP

(57) ABSTRACT

A probe that facilitates the creation of circumferential lesions in bodily tissue. The probe includes a relatively short shaft and a loop-like structure that supports electrodes or other operative elements against the bodily tissue.

29 Claims, 3 Drawing Sheets

U.S. PATENT DOCUMENTS

| | | | |
|---|---|---|---|
| 4,651,734 | A | 3/1987 | Doss et al. |
| 4,681,122 | A | 7/1987 | Winters et al. |
| 4,765,331 | A | 8/1988 | Petruzzi et al. |
| 4,800,899 | A | 1/1989 | Elliott |
| 4,920,978 | A | 5/1990 | Colvin |
| 5,002,561 | A | 3/1991 | Fisher |
| 5,013,312 | A | 5/1991 | Parins et al. |
| 5,078,716 | A | 1/1992 | Doll |
| 5,088,997 | A | 2/1992 | Delahuerga et al. |
| 5,092,314 | A | 3/1992 | Zeitels |
| 5,108,391 | A | 4/1992 | Flachenecker et al. |
| 5,122,137 | A | 6/1992 | Lennox |
| 5,131,379 | A | 7/1992 | Sewell, Jr. |
| 5,147,357 | A | 9/1992 | Rose et al. |
| 5,244,462 | A | 9/1993 | Delahuerga et al. |
| 5,249,121 | A | 9/1993 | Baum et al. |
| 5,263,493 | A | 11/1993 | Avitall |
| 5,277,201 | A | 1/1994 | Stern |
| 5,290,286 | A | 3/1994 | Parins |
| 5,318,564 | A | 6/1994 | Eggers |
| 5,324,288 | A | 6/1994 | Billings et al. |
| 5,342,356 | A | 8/1994 | Ellman et al. |
| 5,370,650 | A | 12/1994 | Tovey et al. |
| 5,381,896 | A | 1/1995 | Simons |
| 5,383,876 | A | 1/1995 | Nardella |
| 5,401,274 | A | 3/1995 | Kusunoki |
| 5,403,342 | A | 4/1995 | Tovey et al. |
| 5,415,656 | A | 5/1995 | Tihon et al. |
| 5,423,810 | A | 6/1995 | Goble et al. |
| 5,437,664 | A | 8/1995 | Cohen et al. |
| 5,437,665 | A | 8/1995 | Munro |
| 5,443,463 | A | 8/1995 | Stern et al. |
| 5,445,638 | A | 8/1995 | Rydell et al. |
| 5,451,224 | A | 9/1995 | Goble et al. |
| 5,456,699 | A | 10/1995 | Armstrong |
| 5,486,173 | A | 1/1996 | Vancaillie |
| 5,505,730 | A | 4/1996 | Edwards |
| 5,562,720 | A | 10/1996 | Stern et al. |
| 5,569,242 | A | 10/1996 | Lax et al. |
| 5,571,098 | A | 11/1996 | Domankevitz et al. |
| 5,582,609 | A | 12/1996 | Swanson |
| 5,624,454 | A | 4/1997 | Palti |
| 5,626,607 | A | 5/1997 | Malecki et al. |
| 5,630,426 | A | 5/1997 | Eggers et al. |
| 5,658,280 | A | 8/1997 | Issa |
| 5,676,678 | A | 10/1997 | Schad |
| 5,681,282 | A | 10/1997 | Eggers et al. |
| 5,683,366 | A | 11/1997 | Eggers et al. |
| 5,687,723 | A | 11/1997 | Avitall |
| 5,688,266 | A | 11/1997 | Edwards et al. |
| 5,697,536 | A | 12/1997 | Eggers et al. |
| 5,697,882 | A | 12/1997 | Eggers et al. |
| 5,697,909 | A | 12/1997 | Eggers et al. |
| 5,702,371 | A | 12/1997 | Bierman |
| 5,702,438 | A | 12/1997 | Avitall |
| 5,720,745 | A | 2/1998 | Farin et al. |
| 5,730,704 | A | 3/1998 | Avitall |
| 5,733,280 | A | 3/1998 | Avitall |
| 5,738,683 | A | 4/1998 | Osypka |
| 5,741,249 | A * | 4/1998 | Moss et al. .................. 606/41 |
| 5,746,748 | A | 5/1998 | Steinberg |
| 5,788,688 | A | 8/1998 | Bauer et al. |
| 5,823,956 | A | 10/1998 | Roth et al. |
| 5,830,183 | A | 11/1998 | Krieger |
| 5,833,690 | A | 11/1998 | Yates et al. |
| 5,836,947 | A | 11/1998 | Fleischman et al. |
| 5,868,742 | A | 2/1999 | Manes et al. |
| 5,871,523 | A | 2/1999 | Fleischman et al. |
| 5,895,386 | A | 4/1999 | Odell et al. |
| 5,908,420 | A | 6/1999 | Parins et al. |
| 5,947,964 | A | 9/1999 | Eggers et al. |
| 6,012,457 | A | 1/2000 | Lesh |
| 6,024,740 | A | 2/2000 | Lesh |
| 6,064,902 | A | 5/2000 | Haissaguerre et al. |
| 6,071,281 | A | 6/2000 | Burnside et al. |
| 6,117,101 | A | 9/2000 | Diederich |
| 6,142,994 | A | 11/2000 | Swanson et al. |
| 6,152,920 | A | 11/2000 | Thompson et al. |
| 6,161,543 | A | 12/2000 | Cox et al. |
| 6,164,283 | A | 12/2000 | Lesh |
| 6,171,306 | B1 * | 1/2001 | Swanson et al. .............. 606/41 |
| 6,214,002 | B1 | 4/2001 | Fleischman |
| 6,237,605 | B1 | 5/2001 | Vaska et al. |
| 6,254,599 | B1 | 7/2001 | Lesh et al. |
| 6,290,699 | B1 | 9/2001 | Hall et al. |
| 6,311,692 | B1 | 11/2001 | Vaska et al. |
| 6,314,962 | B1 | 11/2001 | Vaska et al. |
| 6,314,963 | B1 | 11/2001 | Vaska et al. |
| 6,325,797 | B1 | 12/2001 | Stewart et al. |
| 2001/0007070 | A1 | 7/2001 | Stewart et al. |

* cited by examiner

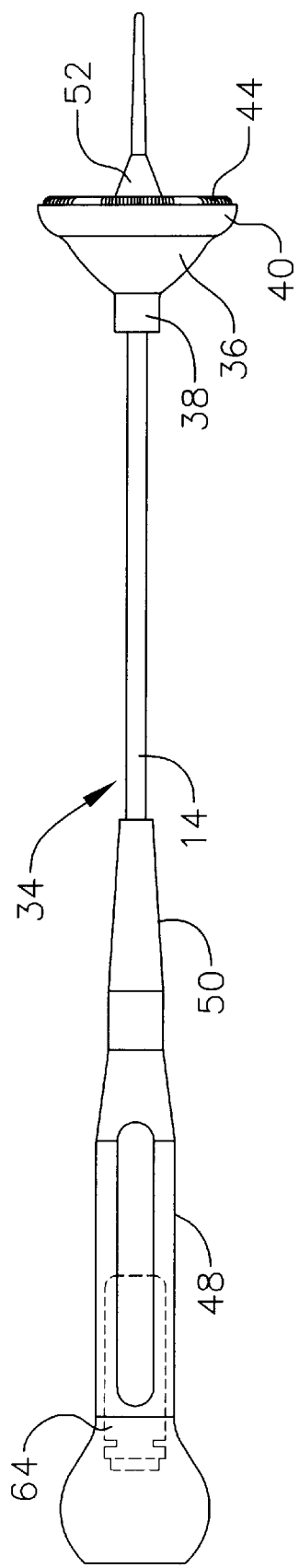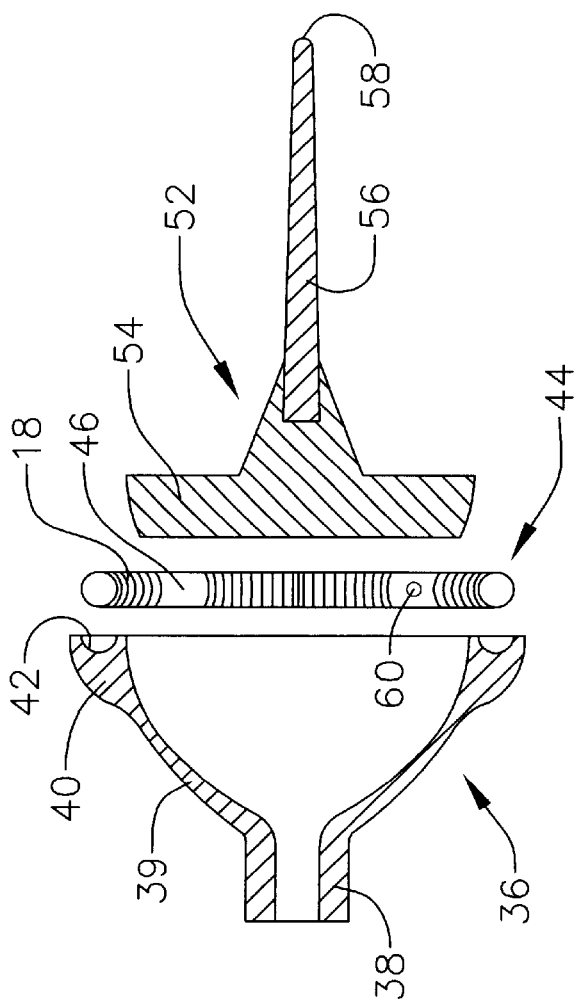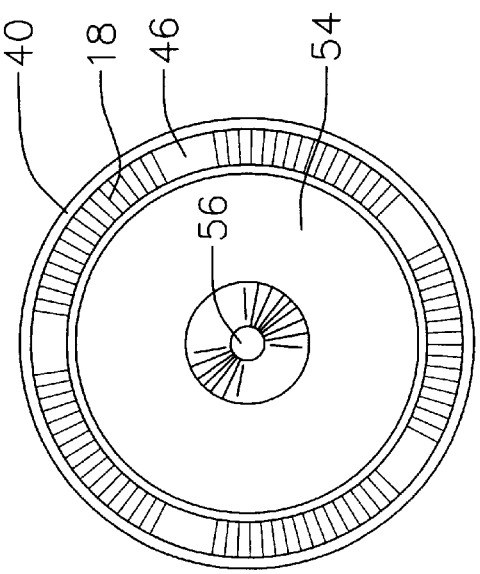

SURGICAL PROBE FOR SUPPORTING DIAGNOSTIC AND THERAPEUTIC ELEMENTS IN CONTACT WITH TISSUE IN OR AROUND BODY ORIFICES

CROSS-REFERENCE TO RELATED APPLICATIONS

This application is a continuation-in-part of U.S. application Ser. No. 08/949,117, filed Oct. 10, 1997, now U.S. Pat. No. 6,152,920 and U.S. application Ser. No. 09/072,872, filed May 5, 1998, now U.S. Pat. No. 6,142,994 each of which is incorporated herein by reference.

BACKGROUND OF THE INVENTIONS

1. Field of Inventions

The present inventions relate generally to surgical probes that support one or more diagnostic or therapeutic elements in contact with body tissue and, more particularly, to surgical probes that support one or more diagnostic or therapeutic elements in contact with bodily orifices and the tissue surrounding such orifices.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do.

Maze-like procedures have also been developed utilizing catheters which can form lesions on the endocardium (the lesions being 1 to 15 cm in length and of varying shape) to effectively create a maze for electrical conduction in a predetermined path. The formation of these lesions by soft tissue coagulation (also referred to as "ablation") can provide the same therapeutic benefits that the complex incision patterns that the surgical maze procedure presently provides.

Catheters used to create lesions typically include a relatively long and relatively flexible body portion that has a soft tissue coagulation electrode on its distal end and/or a series of spaced tissue coagulation electrodes near the distal end. The proximal end of the flexible body is typically connected to a handle which includes steering controls. The portion of the catheter body portion that is inserted into the patient is typically from 23 to 55 inches in length and there may be another 8 to 15 inches, including a handle, outside the patient. The length and flexibility of the catheter body allow the catheter to be inserted into a main vein or artery (typically the femoral artery), directed into the interior of the heart, and then manipulated such that the coagulation electrode contacts the tissue that is to be ablated. Linear and curvilinear lesions can then be created by dragging a single electrode or by applying power (preferably simultaneously) to the series of spaced electrodes.

Catheter-based soft tissue coagulation has proven to be a significant advance in the medical arts generally and in the treatment of cardiac conditions in particular. Nevertheless, the inventors herein have determined that catheter-based procedures are not appropriate in every situation and that conventional catheters are not capable of reliably forming all types of lesions. For example, one lesion that has proven to be difficult to form with conventional catheter devices is the circumferential lesion that is used to isolate the pulmonary vein and cure ectopic atrial fibrillation. Lesions that isolate the pulmonary vein may be formed within the pulmonary vein itself or in the tissue surrounding the pulmonary vein. These circumferential lesions are formed by dragging a tip electrode around the pulmonary vein or by creating a group of interconnected curvilinear lesions one-by-one around the pulmonary vein. Such techniques have proven to be less than effective because they are slow and gaps of conductive tissue can remain after the procedure. It can also be difficult to achieve the adequate tissue contact with conventional catheters.

Accordingly, the inventors herein have determined that a need exists for structures that can be used to create circumferential lesions within or around bodily orifices and, in the context of the treatment of atrial fibrillation, within or around the pulmonary vein.

SUMMARY OF THE INVENTION

Accordingly, the general object of the present inventions is to provide a device that avoids, for practical purposes, the aforementioned problems. In particular, one object of the present inventions is to provide a device that can be used to create circumferential lesions in or around the pulmonary vein and other bodily orifices in a more efficient manner than conventional apparatus.

In order to accomplish some of these and other objectives, a surgical probe in accordance with one embodiment of a present invention includes a relatively short shaft, a support structure associated with the distal end of the relatively short shaft, and an operative element supported on the support structure. The support structure in one preferred implementation includes a loop-like portion that supports the operative element, such as a plurality of electrodes, in a plane that is perpendicular to the longitudinal axis of the shaft. The support structure is also preferably bendable.

Such a probe provides a number of advantages over conventional apparatus. For example, the present surgical probe may be used during open heart surgery or in less invasive procedures where access to the heart is obtained via a thoracostomy, thoracotomy or median sternotomy. The relatively short shaft and manner in which access is obtained allows the electrodes to be easily inserted into the heart and placed against the target tissue with the desired level of contact, thereby eliminating many of the problems associated with catheter-based procedures. The loop-like portion can be used to position the electrodes within or around the pulmonary vein (or other orifice in other procedures) so that a circumferential lesion can be created in one step. In addition, the flexibility of the support structure allows the physician to achieve the appropriate level of tissue contact, even when the shaft is not perfectly perpendicular to the target tissue area and when the target tissue area is somewhat uneven.

In order to accomplish some of these and other objectives, a surgical probe in accordance with one embodiment of a present invention includes a relatively short shaft, a support structure, an operative element supported on the support structure, and an anchor member associated with at least one of the relatively short shaft and the support structure and extending distally therefrom. Such a probe provides a number of advantages over conventional apparatus. For example, the anchor member can be inserted into a bodily orifice such as the pulmonary vein in order accurately position the operative element relative to the orifice. In a preferred implementation, the support structure includes a loop-like portion that supports a plurality of electrodes. Here, the anchor member can be used to center the loop-like portion and electrodes with respect to the pulmonary vein or other bodily orifice so that a circumferential lesion can be quickly and accurately formed in or around the pulmonary vein or other bodily orifice.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 5 is a side view of a surgical probe in accordance with a preferred embodiment of a present invention.

FIG. 6 is an end view of the surgical probe illustrated in FIG. 5.

FIG. 7 is an exploded section view of the distal portion of the probe illustrated in FIG. 5.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Surgical Probe Structures

II. Electrodes, Temperature Sensing and Power Control

The section titles and overall organization of the present detailed description are for the purpose of convenience only and are not intended to limit the present inventions.

This specification discloses a number of probe structures, mainly in the context of cardiac ablation, because the structures are well suited for use with myocardial tissue. For example, the present inventions are designed to produce intimate tissue contact with target substrates associated with arrhythmias such as atrial fibrillation. One application is the creation of lesions within or around the pulmonary vein to treat ectopic atrial fibrillation. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus and other solid organs.

1. Surgical Probe Structures

Figure 1:
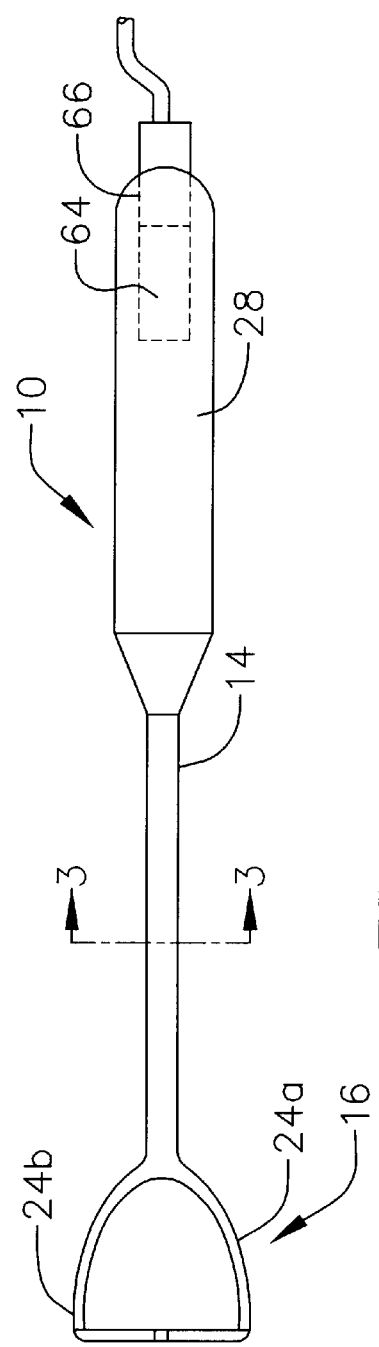
FIG. 1 is a side view of a surgical probe in accordance with a preferred embodiment of a present invention.
Figure 2:
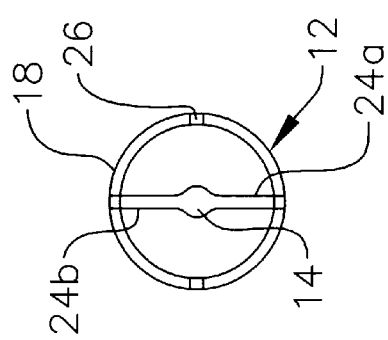
FIG. 2 is an end view of the surgical probe illustrated in FIG. 1.
Figure 3:
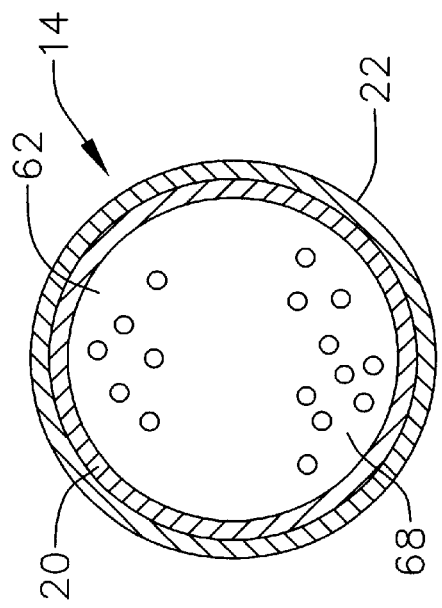
FIG. 3 is a section view taken along line 3—3 in FIG. 1.

As illustrated for example in FIGS. 1–3, a surgical probe 10 for positioning an operative element 12 within a patient includes a relatively short shaft 14 and a structure, such as a spline assembly 16, associated with the distal end of the shaft for supporting the operative element. Here, the operative element is in the form of a plurality of spaced electrodes 18. The relatively short shaft 14 is preferably between approximately 4 and 18 inches in length, and is preferably 8 inches in long, while the outer diameter of the shaft is preferably between approximately 6 and 24 French. In the exemplary embodiment illustrated in FIGS. 1–3, the shaft 14 consists of a hypotube 20 with and outer polymer coating 22. The spline assembly 16, which is preferably readily bendable, consists of two spline legs 24a and 24b and an annular member 26 which supports the plurality of electrodes 18. Other spline assemblies, such as spline assemblies that include three to ten equally spaced spline legs, can also be used. The diameter of the annular member 26 may vary to suit particular needs. For example, an annular member intended for use with pulmonary veins would have a diameter of about 1.0 cm to about 3.0 cm. A handle 28 may be provided on the proximal end of the shaft 14.

The spline assembly 16 has a predetermined use configuration which positions the electrodes 18 or other operative element in a circular (as shown), oval, triangular, rectangular or other closed loop-like shape that faces in the distal direction and defines an open region therewithin. In the illustrated embodiment, the electrodes 18 are supported in a plane perpendicular to the longitudinal axis of the shaft 14. The electrodes 18 may be placed directly in contact with the targeted tissue area by a physician during a surgical procedure, such as open heart surgery. The flexibility of spline assembly 16 allows the physician to achieve the appropriate level of tissue contact, even when the shaft 14 is not perfectly perpendicular to the target tissue area and when the target tissue area is somewhat uneven. As a result, the physician can form a lesion that extends completely around the pulmonary vein or other bodily orifice by simply inserting the distal portion of the probe 10 into the patient, positioning electrodes in or around the bodily orifice, and applying power to the electrodes.

Force is applied through the shaft 14 and the spline assembly 16 in order to achieve the appropriate level of tissue contact. Thus, the shaft 14 should be sufficiently strong to prevent collapse when the force is applied and is preferably relatively stiff. Although bendable enough to allow it be reoriented relative to the shaft 14 and to conform to the desired anatomical structure, the spline assembly 16 should also be strong enough to allow the physician to apply the appropriate level of force. The spline assembly 16 in the embodiment illustrated in FIGS. 13 can also be relatively stiff if applications require.

As used herein the phrase "relatively stiff" means that the shaft 14 (or other structural element) is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial. Rigid and somewhat flexible shafts are preferably formed from stainless steel, while malleable shafts are formed from annealed stainless steel.

One method of quantifying the flexibility of a shaft, be it shafts in accordance with the present inventions or the shafts of conventional catheters, is to look at the deflection of the shaft when one end is fixed in cantilever fashion and a force normal to the longitudinal axis of the shaft is applied somewhere between the ends. Such deflection ($\sigma$) is expressed as follows:

$$\sigma = WX^2(3L-X)/6EI$$

where:
W is the force applied normal to the longitudinal axis of the shaft,
L is the length of the shaft,
X is the distance between the fixed end of the shaft and the applied force,
E is the modulous of elasticity, and
I is the moment of inertia of the shaft.

When the force is applied to the free end of the shaft, deflection can be expressed as follows:

$$\sigma = WL^3/3EI$$

Assuming that W and L are equal when comparing different shafts, the respective E and I values will determine how much the shafts will bend. In other words, the stiffness of a shaft is a function of the product of E and I. This product is referred to herein as the "bending modulus." E is a property of the material that forms the shaft, while I is a function of shaft geometry, wall thickness, etc. Therefore, a shaft formed from relatively soft material can have the same bending modulus as a shaft formed from relatively hard material, if the moment of inertia of the softer shaft is sufficiently greater than that of the harder shaft.

For example, a relatively stiff 2 inch shaft (either malleable or somewhat flexible) would have a bending modulus of at least approximately 1 lb.-in.$^2$ Preferably, a relatively stiff 2 inch shaft will have a bending modulus of between approximately 3 lb.-in.$^2$ and approximately 50 lb.-in.$^2$. By comparison, 2 inch piece of a conventional catheter shaft, which must be flexible enough to travel through veins, typically has bending modulus between approximately 0.1 lb.-in.$^2$ and approximately 0.3 lb.-in.$^2$. It should be noted that the bending modulus ranges discussed here are primarily associated with initial deflection. In other words, the bending modulus ranges are based on the amount of force, applied at and normal to the free end of the longitudinal axis of the cantilevered shaft, that is needed to produce 1 inch of deflection from an at rest (or no deflection) position.

As noted above, the deflection of a shaft depends on the composition of the shaft as well as its moment of inertia. The shaft could be made of elastic material, plastic material, elasto-plastic material or a combination thereof. By designing the shaft 14 to be relatively stiff (and preferably malleable), the present surgical probe is better adapted to the constraints encountered during the surgical procedure. The force required to bend a relatively stiff 2 inch long shaft should be in the range of approximately 1.5 lbs. to approximately 12 lbs. By comparison, the force required to bend a 2 inch piece of conventional catheter shaft should be between approximately 0.2 lb. to 0.25 lb. Again, such force values concern the amount of force, applied at and normal to the free end of the longitudinal axis of the cantilevered shaft, that is needed to produce 1 inch of deflection from an at rest (or no deflection) position.

Ductile materials are preferable in many applications because such materials can deform plastically before failure due to fracturing. Materials are classified as either ductile or brittle, based upon the percentage of elongation when the fracture occurs. A material with more than 5 percent elongation prior to fracture is generally considered ductile, while a material with less than 5 percent elongation prior to fracture is generally considered brittle. Material ductility can be based on a comparison of the cross sectional area at fracture relative to the original cross area. This characteristic is not dependent on the elastic properties of the material.

Alternatively, the shaft 14 could be a mechanical component similar to shielded (metal spiral wind jacket) conduit or flexible Loc-Line®, which is a linear set of interlocking ball and socket linkages that can have a center lumen. These would be hinge-like segmented sections linearly assembled to make the shaft.

Figure 4:
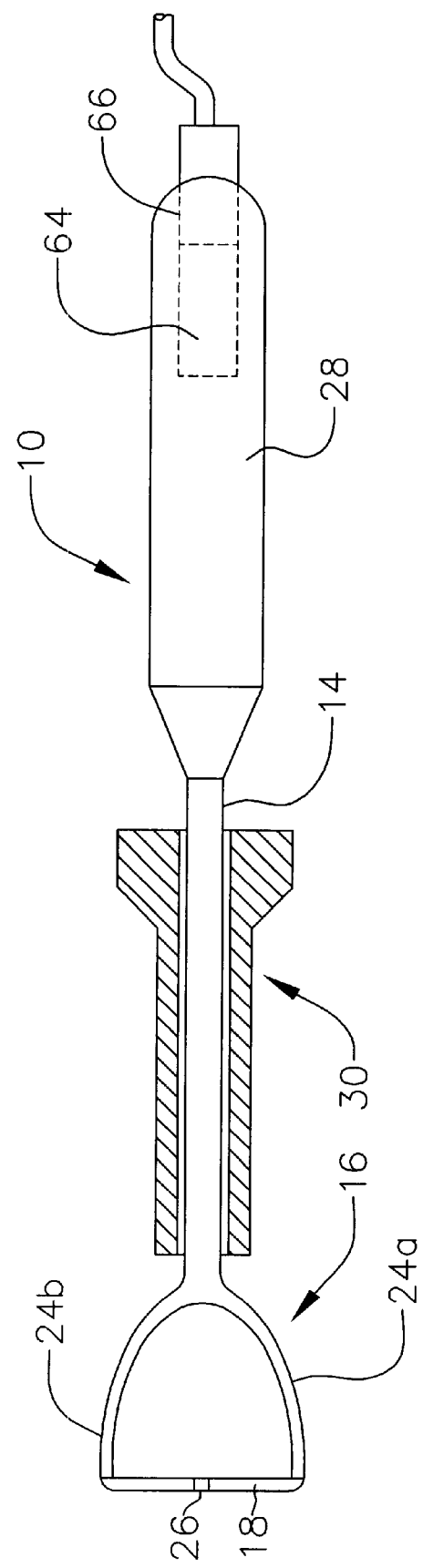
FIG. 4 is a side view of a surgical probe in accordance with a preferred embodiment of a present invention.

In those instances where access is to be obtained by way of a less invasive procedure, such as thoracotomy, median sternotomy, or thoracostomy, a tubular member may be provided which covers a portion of the shaft 14 and is also slidable relative thereto. A suitable tubular member 30 is illustrated in FIG. 4. Here, the spline assembly 16 must be extremely bendable and adapted to collapse (the insertion configuration) in response to movement of the substantially tubular member 30 in the distal direction and to expand to the predetermined use configuration when the substantially tubular member is moved in the proximal direction. The tubular member 30 preferably includes a raised gripping surface 32.

A bendable spline assembly 16 that is adapted to collapse and expand, such as the spline assembly illustrated in FIG. 4, is preferably made from resilient, inert wire, like nickel titanium (commercially available as Nitinol material) or 17-7 stainless steel. However, resilient injection molded inert plastic can also be used. The wire or molded plastic is covered by suitable biocompatible thermoplastic or elastomeric material such as PEBAX® or Pellethane®. Preferably, the various portions of the spline assemblies comprises a thin, rectilinear strips of resilient metal or plastic material. Still, other cross-sectional and longitudinal configurations can be used. For example, the spline legs can decrease in cross-sectional area in a distal direction, by varying, e.g., thickness or width or diameter (if round), to provide variable stiffness along its length. Variable stiffness can also be imparted by composition changes in materials or by different material processing techniques.

The exemplary tubular member 30 illustrated in FIG. 4 is preferably in the form of a relatively thin cylindrical sheath (e.g., with a wall thickness of about 0.005 inch) and has an outer diameter which is preferably less than 0.180 inch. The sheath material is preferably also lubricious, to reduce friction during movement of the sheath relative to the shaft 14 and spline assembly 16. For example, materials made from polytetrafluoroethylene (PTFE) can be used for the sheath. The distal end of the sheath should be relatively flexible to prevent injury. If necessary, additional stiffness can be imparted to the remaining portion of the sheath by lining the sheath with a braided material coated with PEBAX® material (comprising polyethel block amide related to nylon). Other compositions made from PTFE braided with a stiff outer layer and other lubricious materials can be used. Alternatively, the tubular member 30 may be relatively stiff and formed from the materials described above with respect to the shaft 14.

Another surgical probe, which is generally represented by reference numeral 34, is illustrated for example in FIGS. 5–7. Like the probe illustrated in FIGS. 1–3, surgical probe 34 includes a relatively short shaft 14 that is relatively stiff (preferably malleable) and a distal structure that supports an operative element, such as a plurality of spaced electrodes 18. Here, the distal structure is in the form of an elastomeric frusto-conical support structure 36 that can flex and deform as needed to conform to the target anatomical structure, such as the pulmonary vein ostium. The exemplary support structure 36 includes a base member 38 that is secured to the shaft 14, preferably with adhesive, a wall 39 that defines an open area therewithin, and a support member 40 with an annular seat 42. An annular electrode assembly 44 is mounted within the annular seat 42 and is secured thereto with adhesive. The annular electrode assembly 44 includes a tubular body 46 that carries the plurality of spaced electrodes 18. The exemplary probe 34 also includes a handle 48 with a strain relief element 50.

The elastomeric support structure 36 is not limited to the illustrated frusto-conical shape. Other shapes, such as a zone or segment of a sphere, catenoid, paraboloid, or cylinder may also be used. In other words, the support structure is preferably an open structure including a wall that surrounds an open area. Nevertheless, other flexible structures which can support the annular electrode assembly 44 (or electrode assembly of another closed shape) in the desired orientation may be used. A balloon-like structure having the desired shape is one example of such an alternative flexible structure.

Like the spline assembly 16 illustrated in FIGS. 1–4, the elastomeric support structure 36 positions the electrodes 18 or other operative elements in a circular (as shown), oval, rectangle, triangle or other closed loop-like shape that faces in the distal direction. Here too, the electrodes 18 may be placed directly in contact with the targeted tissue area by a physician during a surgical procedure, such as open heart surgery, and the flexibility of support structure 36 allows the physician to achieve the appropriate level of tissue contact, even when the shaft 14 is not perfectly perpendicular to the target tissue area and the tissue surface is somewhat irregular.

In the preferred embodiment illustrated in FIGS. 5–7, an anchor assembly 52 is secured within the distal region of the support structure 36. The exemplary anchor assembly 52 includes a relatively stiff base member 54 and a soft, flexible anchor 56 with an atraumatic blunt tip 58 that is supported on the base member. The anchor 56 may be whatever length is appropriate for the intended use. For example, in pulmonary vein applications, approximately 1 to 3 inches is appropriate. During use, the anchor 56 may be positioned within a bodily orifice, such as the pulmonary vein, thereby centering the electrode assembly 44 relative to the orifice and insuring accurate positioning of the electrodes. This allows a circumferential lesion to be quickly and accurately created in or around the pulmonary vein or other orifice. The anchor assembly 52 may also be used in combination with the probes illustrated in FIGS. 1–4, albeit in a slightly modified form so that it can be secured to the spline legs 24a and 24b.

In addition to supporting the anchor 56, the base member 54 maintains the shape of the distal region of the support structure 36. Although the distal region of the support member 36 in the illustrated embodiment has a circular shape, as does the base member 54 (FIG. 6), ovals, rectangles, triangles and other shapes may also be employed as applications require. Because the base member 54 maintains the shape, the support structure 36 can be made softer than it could be otherwise, especially the wall 39 between the base member 38 and the support member 40, thereby increasing the flexibility of the support structure and its ability to flex as needed during surgical procedures.

Alternatively, for those instances where it would be desirable for the distal portion of the support structure 36 to be deformable, the anchor assembly 52 can be reconfigured such that the base member 54 is secured to the shaft 14 and the diameter of the base member is reduced.

With respect to materials and manufacture, the exemplary support structure 36 may be formed from any suitable elastomeric material. Preferably, the support structure 36 is formed from a low durometer polymer, such as 45D to 55D polyurethane or Santoprene®. The tubular body 46 is preferably a flexible PEBAX® extrusion that is bent into and fixed in the annular shape after the electrodes 18 have been mounted thereon. An aperture 60 is provided in the tubular body 46 for the wires that extend from the electrodes 18 and associated temperature sensors. The wires may be bundled and placed within a tubular member (not show) that extends from the aperture to the shaft 14. The anchor base 54 and anchor 56 are also preferably formed from a low durometer polymer, such as 45D to 55D polyurethane or Santoprene®.

II. Electrodes, Temperature Sensing and Power Control

In each of the preferred embodiments, the operative element is a plurality of spaced electrodes 18. However, other operative elements, such as lumens for chemical ablation, laser arrays, ultrasonic transducers, microwave electrodes, and D.C. hot wires, may be substituted for the electrodes. Additionally, although the principal use of the electrodes is to transmit electrical energy and, more particularly, RF energy, to ablate heart tissue, the electrodes can also be used to sense electrical events in tissue. With respect to heart tissue in particular, the electrodes can serve to transmit electrical pulses to measure the impedance of heart tissue, to pace heart tissue, or to assess tissue contact using conventional pacing and sensing techniques. Once the physician establishes contact with tissue in the desired heart region, the physician applies ablating energy to the electrodes.

The spaced electrodes 18 are preferably in the form of wound, spiral coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. A preferred coil electrode is disclosed in U.S. Pat. No. 5,797,905.

The electrodes 18 are electrically coupled to individual wires 62 (FIG. 3) to conduct coagulating energy to them. The wires are passed through a lumen in one of the spline legs 24a and 24b (FIGS. 1–4) or through the open area within the elastomeric support structure 36 (FIGS. 5–7). The wires are then passed in conventional fashion through the shaft 14 into a PC board 64 in the handle 28 (FIGS. 1–4) or 48 (FIGS. 5–7), where they are electrically coupled to a connector 66 that is received in a port on the handle. The connector 66 plugs into a source of RF coagulation energy.

As an alternative, the electrodes 18 may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel or titanium can be applied. The electrodes can also be in the form of helical ribbons. The electrodes can also be formed with a conductive ink compound that is pad printed onto a nonconductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

The flexible electrodes 18 are preferably about 4 mm to about 20 mm in length. In the preferred embodiment, the electrodes are 12.5 mm in length with 1–3 mm spacing, which will result in the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

In the exemplary probe 10 illustrated in FIGS. 1–4, the portion of the electrodes 18 that are not intended to contact tissue may be masked through a variety of techniques with a material that is preferably electrically and thermally insulating. This prevents the transmission of coagulation energy directly into the blood pool and directs the energy directly toward and into the tissue. For example, a layer of UV adhesive (or another adhesive) may be painted on preselected portions of the electrodes to insulate the portions of the electrodes not intended to contact tissue. Deposition techniques may also be implemented to position a conductive surface only on those portions of the assembly intended to contact tissue. Alternatively, a coating may be formed by dipping the electrodes in PTFE material.

The electrodes 18 may be operated in a uni-polar mode, in which the soft tissue coagulation energy emitted by the electrodes is returned through an indifferent patch electrode (not shown) externally attached to the skin of the patient. Alternatively, the electrodes may be operated in a bi-polar mode, in which energy emitted by one or more electrodes is returned through other electrodes. The amount of power required to coagulate tissue ranges from 5 to 150 w.

A plurality of temperature sensors (not shown), such as thermocouples or thermistors, may be located on, under, abutting the longitudinal end edges of, or in between, the electrodes 18. Preferably, the temperature sensors are located at the longitudinal edges of the electrodes 18 on the distally facing side of the annular member 26 and tubular body 46. In some embodiments, a reference thermocouple may also be provided. For temperature control purposes, signals from the temperature sensors are transmitted to the source of coagulation energy by way of wires 68 (FIG. 3) that are also connected to the PC board 64. A suitable power control arrangement is disclosed in aforementioned U.S. application Ser. No. 09/072,872, which is entitled "Surgical Method and Apparatus For Positioning a Diagnostic of Therapeutic Element Within the Body."

Finally, the electrodes 18 and temperature sensors can include a porous material coating, which transmits coagulation energy through an electrified ionic medium. For example, as disclosed in U.S. application Ser. No. 08/879, 343, filed Jun. 20, 1997, entitled "Surface Coatings For Catheters, Direct Contacting Diagnostic and Therapeutic Devices," electrodes and temperature sensors may be coated with regenerated cellulose, microporous polymers (such as polysulfone), hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims set forth below.

We claim:

1. A surgical probe, comprising:
    a relatively short shaft defining a distal end, a proximal end and a longitudinal axis;
    a support structure associated with the distal end of the relatively short shaft having a distal portion defining a closed shape and lying in a plane oriented substantially perpendicular to the longitudinal axis; and
    an operative element supported on the support structure.

2. A surgical probe as claimed in claim 1, wherein the relatively short shaft is relatively stiff.

3. A surgical probe as claimed in claim 1, wherein the relatively short shaft is malleable.

4. A surgical probe as claimed in claim 1, wherein the distal portion of the support structure defines a circular shape.

5. A surgical probe as claimed in claim 1, wherein the support structure is bendable.

6. A surgical probe as claimed in claim 5, wherein the support structure comprises a spline assembly.

7. A surgical probe as claimed in claim 6, wherein the spline assembly comprises at least two spline legs and an annular member supported by the spline legs.

8. A surgical probe as claimed in claim 5, wherein the support structure comprises an elastomeric member including a wall defining an open area.

9. A surgical probe as claimed in claim 8, wherein the elastomeric member defines a generally frusto-conical shape.

10. A surgical probe as claimed in claim 8, wherein the wall includes a distally facing seat and the operative element is located at least partially within the seat.

11. A surgical probe as claimed in claim 8, wherein the wall defines a distal region, the surgical probe further comprising:

a relatively stiff member positioned within the open area at the distal region of the wall.

12. A surgical probe as claimed in claim 1, wherein the operative element comprises a plurality of electrodes.

13. A surgical probe as claimed in claim 1, further comprising:

an anchor associated with at least one of the relatively short shaft and the support structure and extending distally therefrom.

14. A surgical probe, comprising:

a relatively short shaft defining a distal end, a proximal end and a longitudinal axis;

a loop-like support structure associated with the distal end of the relatively short shaft; and an operative element supported on the support structure.

15. A surgical probe as claimed in claim 14, wherein the relatively short shaft is relatively stiff.

16. A surgical probe as claimed in claim 14, wherein the relatively short shaft is malleable.

17. A surgical probe as claimed in claim 14, wherein the loop-like structure comprises an annular structure.

18. A surgical probe as claimed in claim 14, further comprising:

a bendable structure supporting the loop-like structure on the relatively short shaft.

19. A surgical probe as claimed in claim 18, wherein the bendable structure comprises a spline assembly.

20. A surgical probe as claimed in claim 18, wherein the bendable structure comprises an elastomeric member including a wall defining an open area.

21. A surgical probe as claimed in claim 14, wherein the operative element comprises a plurality of electrodes.

22. A surgical probe as claimed in claim 14, further comprising:

an anchor associated with the loop-like structure and extending distally therefrom.

23. A surgical probe as claimed in claim 14, wherein the loop-like structure is located in a plane substantially perpendicular to the longitudinal axis.

24. A surgical probe, comprising:

a relatively short shaft defining a distal end, a proximal end and a longitudinal axis;

a support structure associated with the distal end of the relatively short shaft;

an operative element supported on the support structure; and an anchor member associated with at least one of the relatively short shaft and the support structure and extending distally therefrom.

25. A surgical probe as claimed in claim 24, wherein the anchor member is associated with the support structure.

26. A surgical probe as claimed in claim 24, wherein the anchor member includes a flexible distal portion.

27. A surgical probe as claimed in claim 24, wherein the support structure comprises a flexible member including a wall defining an open area and a distal region and the anchor member includes a base member positioned within the open area.

28. A surgical probe as claimed in claim 24, wherein the support structure includes a distal portion defining a closed shape and lying in a plane substantially perpendicular to the longitudinal axis.

29. A surgical probe as claimed in claim 24, wherein the operative element comprises a plurality of electrodes.

* * * * *